(12) United States Patent
Yang et al.

(10) Patent No.: US 11,884,628 B2
(45) Date of Patent: Jan. 30, 2024

(54) METHOD FOR SYNTHESIZING LACTAM DERIVATIVES WITHOUT USE OF CATALYST

(71) Applicant: Guizhou University, Guiyang (CN)

(72) Inventors: Song Yang, Guiyang (CN); Hu Li, Guiyang (CN); Hongguo Wu, Guiyang (CN)

(73) Assignee: GUIZHOU UNIVERSITY, Guiyang (CN)

(*) Notice: Subject to any disclaimer, the term of this patent is extended or adjusted under 35 U.S.C. 154(b) by 136 days.

(21) Appl. No.: 17/441,287

(22) PCT Filed: Aug. 22, 2019

(86) PCT No.: PCT/CN2019/102066
§ 371 (c)(1),
(2) Date: Sep. 21, 2021

(87) PCT Pub. No.: WO2020/228170
PCT Pub. Date: Nov. 19, 2020

(65) Prior Publication Data
US 2022/0177429 A1    Jun. 9, 2022

(30) Foreign Application Priority Data
May 16, 2019 (CN) .......................... 201910404767.3

(51) Int. Cl.
*C07D 211/76* (2006.01)
*C07D 207/267* (2006.01)
*C07D 209/46* (2006.01)

(52) U.S. Cl.
CPC ........ *C07D 211/76* (2013.01); *C07D 207/267* (2013.01); *C07D 209/46* (2013.01)

(58) Field of Classification Search
CPC .................................................. C07D 211/76
See application file for complete search history.

(56) References Cited

U.S. PATENT DOCUMENTS 4,331,600 A * 5/1982 Golec, Jr. ............ C07D 209/46
544/63

FOREIGN PATENT DOCUMENTS

| CN | 109942473 A | 6/2019 |
| FR | 3003571 A1 | 9/2014 |

OTHER PUBLICATIONS

Sun "NHC-based coordination polymers as solid molecular catalysts for reductive amination of biomass levulinic acid" Green Chem., 2017, 19, 789.*
International Search Report and Written Opinion dated Feb. 17, 2020, received for PCT Application PCT/CN2019/102066, Filed on Aug. 22, 2019, 11 pages including English Translation.
Li et al., "A Facile Direct Route to N-(Un) substituted Lactams by Cycloamination of Oxocarboxylic Acids without External Hydrogen", Chemsuschem, vol. 12, No. 16, Jul. 17, 2019, pp. 3778-3784.
Wang et al., "Reductive Amination of Levulinic Acid to 5-Methyl-2-pyrrolidone", Biomass Chemical Engineering, vol. 51, No. 2, Mar. 31, 2017, pp. 19-25 (Including English Abstract).
Li et al., "N-Formyl-Stabilizing Quasi-Catalytic Species Afford Rapid and Selective Solvent-Free Amination of Biomass-Derived Feedstocks", Nature Communications, vol. 10, Feb. 11, 2019, pp. 1-13.
Wu et al., "Quasi-Catalytic Approach to N-Unprotected Lactams via Transfer Hydro-amination/Cyclization of Biobased Keto Acids", ACS Sustainable Chemical & Engineering. vol. 7, No. (12) May 24, 2019, pp. 10207-10213.

* cited by examiner

*Primary Examiner* — David K O'Dell
(74) *Attorney, Agent, or Firm* — XSENSUS LLP

(57) ABSTRACT

Disclosed is a simple synthesis method of lactam derivatives, comprising: with formamide functioning as both an amine source and a hydrogen source (hydrolyzed to produce formic acid), carrying out a cycloamination reaction on a raw material keto acid in the absence of a solvent or a catalyst to simply synthesize a lactam derivative. Compared with previous reports, the present disclosure has the following advantages: the time required for the reaction is greatly shortened, the selectivity is remarkably improved, a conversion rate of a keto acid derivative is greater than 99%, and the yield of the lactam derivative can reach 70% to 94%.

5 Claims, 3 Drawing Sheets

METHOD FOR SYNTHESIZING LACTAM DERIVATIVES WITHOUT USE OF CATALYST

CROSS-REFERENCE TO RELATED APPLICATIONS

The present application is based on PCT filing PCT/CN2019/102066, filed Aug. 22, 2019, which claims priority to CN 201910404767.3, filed May 16, 2019, the entire contents of each are incorporated herein by reference.

BACKGROUND OF THE INVENTION

1. Technical Field

The present disclosure relates to a simple method for synthesizing lactam derivatives without use of a catalyst, and in particular to a method where with formamide as both an amine source and a hydrogen source (hydrolyzed to produce formic acid), a keto acid derivative is subjected to a hydro-thermal treatment in the absence of a solvent or an external catalyst and selectively converted into a lactam derivative.

2. Description of Related Art

Lactam derivatives are core groups of a class of natural products and drugs with multiple biological activities. Such nitrogen-containing heterocyclic derivatives are widely used in functional materials and catalysts, and can also be used as important cyclic frameworks of a complex synthesis structure. Pyrrolidone is a type of lactam derivative. Therefore, the exploration of synthetic methods for preparing such five-membered nitrogen-containing heterocyclic derivatives has always attracted wide attention. The market reserves of keto acid derivatives are large, and especially levulinic acid can be directly prepared by acid hydrolysis of biomass carbohydrates. Under the catalysis of a transition metal, levulinic acid and primary amine can undergo reductive amination and ring-closure reactions to obtain N-substituted lactam or pyrrolidone derivatives. For this reason, researchers have adopted different strategies to design and prepare functional catalytic materials that can simplify the reaction process and system.

The selective establishment of C—C and C—N bonds is the most important way to synthesize nitrogen-containing hybrid derivatives. Although the requirements for electron-withdrawing or nucleophilic nitrogen-containing groups are relatively high, it is still interesting to prepare lactam derivatives through metal-catalyzed intramolecular olefin-catalyzed cyclization of primary amines on the basis of the aza-Heck or aza-Wacker mechanism. The lactam derivatives can also be prepared by other reaction routes, such as the reaction of homoenolate and acid-activated imine, carbamylation reduction reaction of intramolecular allyl formamide, Michael/proton transfer/enol lactonization of dicarbonyl chloride, intramolecular dialkenylation reaction of brominated olefins, cyclic amination reaction of propenyl carbamate and urea, etc. However, the smooth implementation of these reactions requires organic solvents and special catalysts/additives. Therefore, it is particularly desired to produce high-value-added lactam derivatives in a sustainable and low-cost manner without use of a catalyst or a solvent.

BRIEF SUMMARY OF THE INVENTION

Directed to the disadvantages of existing catalysts or catalytic systems, such as high production cost, long reaction time, and poor selectivity of lactam derivatives, the present disclosure is intended to simply synthesize a lactam derivative by carrying out a cycloamination reaction on a raw material keto acid with easily available and cheap formamide functioning as both an amine source and a hydrogen source (hydrolyzed to produce formic acid) in the absence of a solvent or a catalyst.

The objective of the present disclosure is reached through the following technical solution:

A simple synthesis method of lactam derivatives, comprising: carrying out a direct addition reaction between a raw material keto acid derivative and formamide functioning as both an amine source and a hydrogen source (hydrolyzed to produce formic acid) in the absence of an organic solvent or a catalyst, and then carrying out formic acid reduction and a ring-closure reaction to obtain a corresponding lactam derivative.

The principle of synthesizing lactam derivatives of the present disclosure: formamide and a keto acid derivative are heated to undergo an addition reaction (C—N coupling) to form a (cyclic) imine intermediate, and then formic acid is generated in situ to provide hydrogen for reduction to obtain a formamide intermediate, and finally a ring-closure reaction is carried out to obtain a lactam derivative. The reaction formula is as follows:

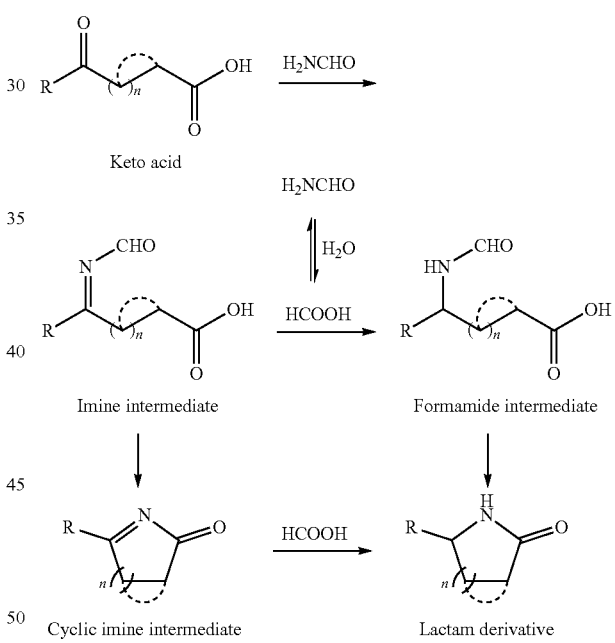

The preparation of lactam derivatives is carried out in an oil bath pot, equipped with a magnetic stirrer; after the oil bath pot is turned on, the reaction system is heated to a specified reaction temperature, the temperature of the oil bath pot is automatically controlled by frequency conversion, and the temperature is controlled by a thermocouple to maintain the reaction temperature. The preparation process of the lactam derivative comprises: putting formamide, water, and a keto acid derivative into a polytetrafluoroethylene-lined stainless steel autoclave, and placing the autoclave in an oil bath pot heated to a specified temperature, wherein the reaction is carried out for 60 to 300 min at a temperature within a range of 140° C. to 180° C.

A molar ratio of the keto acid derivative to the formamide to water is 1:5~15:10~40. In the present disclosure, by controlling the excessive dosage of formamide, the reaction can proceed in a positive direction, and the yield of the lactam derivative reaches at least 70%, thus avoiding the formation of by-products and even carbonization due to the excessively low dosage of formamide. Exceeding the required dosage of the formamide of the present disclosure does not improve the reaction efficiency greatly and causes a great waste of raw materials.

The keto acid derivative includes levulinic acid, 3-(4-chlorobenzoyl)propionic acid, 3-benzoylpropionic acid, 3-(4-fluorobenzoyl)propionic acid, 4-oxo-4-(2-thienyl)butanoic acid, acetobutyric acid, 4-(4-fluorobenzoyl)butyric acid, 4-benzoylbutyric acid, and 2-acetylbenzoic acid. The corresponding lactam derivatives synthesized from the above keto acid derivatives are 5-methyl-2-pyrrolidone, 5-(4-chlorophenyl)-2-pyrrolidone, 5-phenyl-2-pyrrolidone, 5-(4-Fluorophenyl)-2-pyrrolidone, 5-(2-thienyl)-2-pyrrolidone, 6-methyl-2-piperidone, 6-(4-fluorophenyl)-2-piperidine ketone, 6-phenyl-2-piperidone, and 3-methyl-isoindol-1-one in sequence.

The beneficial effects of the present disclosure are as follows.

According to the method of the present disclosure, water is added to promote direct amination and cyclization of the formamide and the keto acid derivative, and then formic acid is generated in situ for the reduction preparation of a corresponding lactam derivative. Compared with previous reports, the present disclosure has the following advantages: the time required for the reaction is greatly shortened, the selectivity is remarkably improved, a conversion rate of a keto acid derivative is greater than 99%, and the yield of the lactam derivative can reach 70% to 94%.

DETAILED DESCRIPTION OF THE INVENTION

The technical solutions of the present disclosure will be further described in detail below in conjunction with the examples, and the examples should not be construed as limitations of the present disclosure.

Example 1

Synthesis of 5-methyl-2-pyrrolidone 2 mmol of levulinic acid, 10 mmol of formamide and 40 mmol of water were put into a 15 mL polytetrafluoroethylene-lined stainless steel reactor, the sealed reactor was then placed in an oil bath pot heated to a predetermined temperature (160° C.) to carry out a reaction for 240 min at 500 r/min, and the reactor was then taken out and cooled to room temperature with tap water. 13 mL of methanol was put into the reactor, the yield of 5-methyl-2-pyrrolidone was measured by GC (gas chromatography), and the conversion rate of levulinic acid was measured by HPLC (liquid chromatography).

Figure 1:
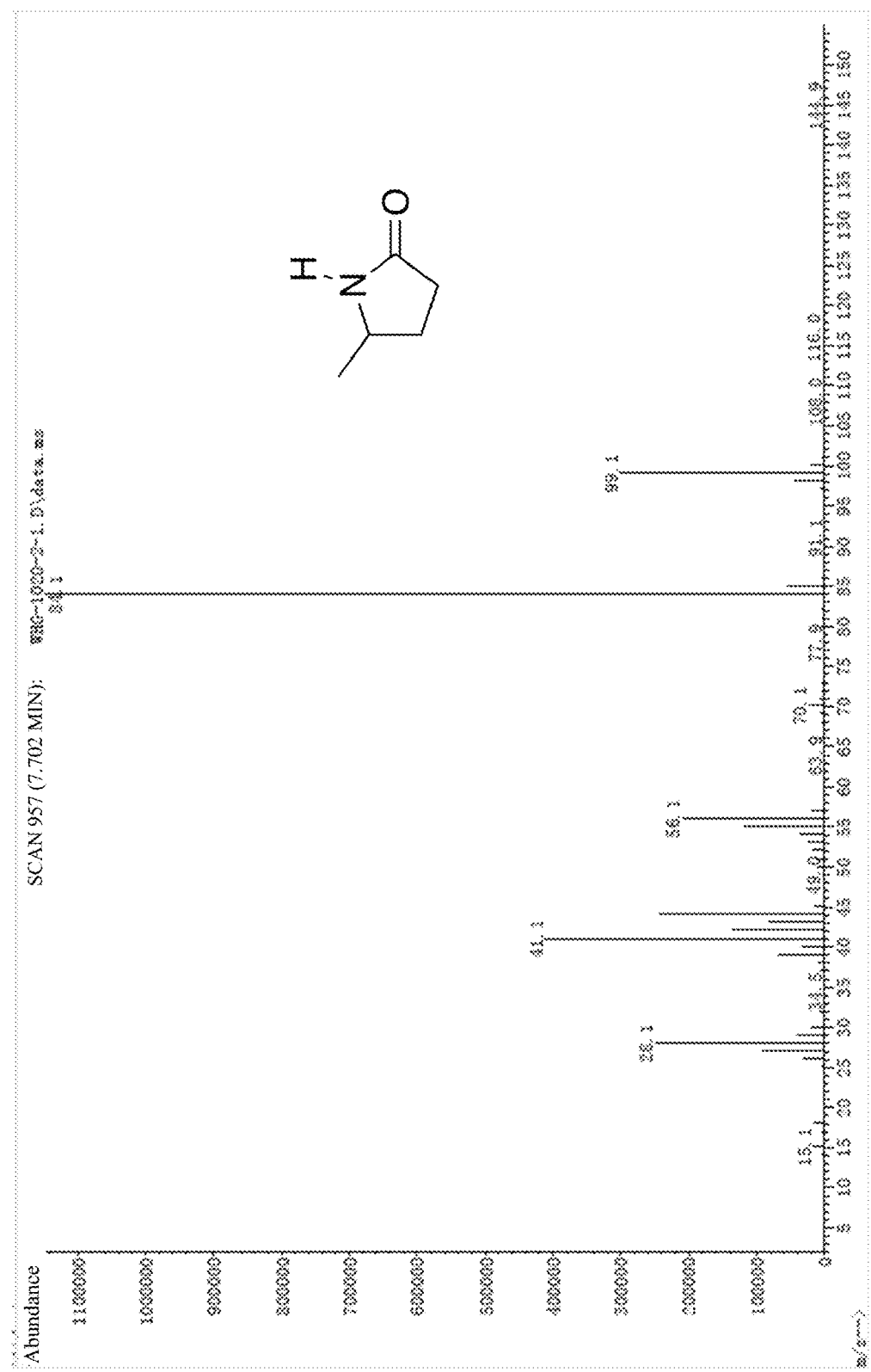
FIG. 1 shows a mass spectrum of 5-methyl-2-pyrrolidone in Example 1.
Figure 2:
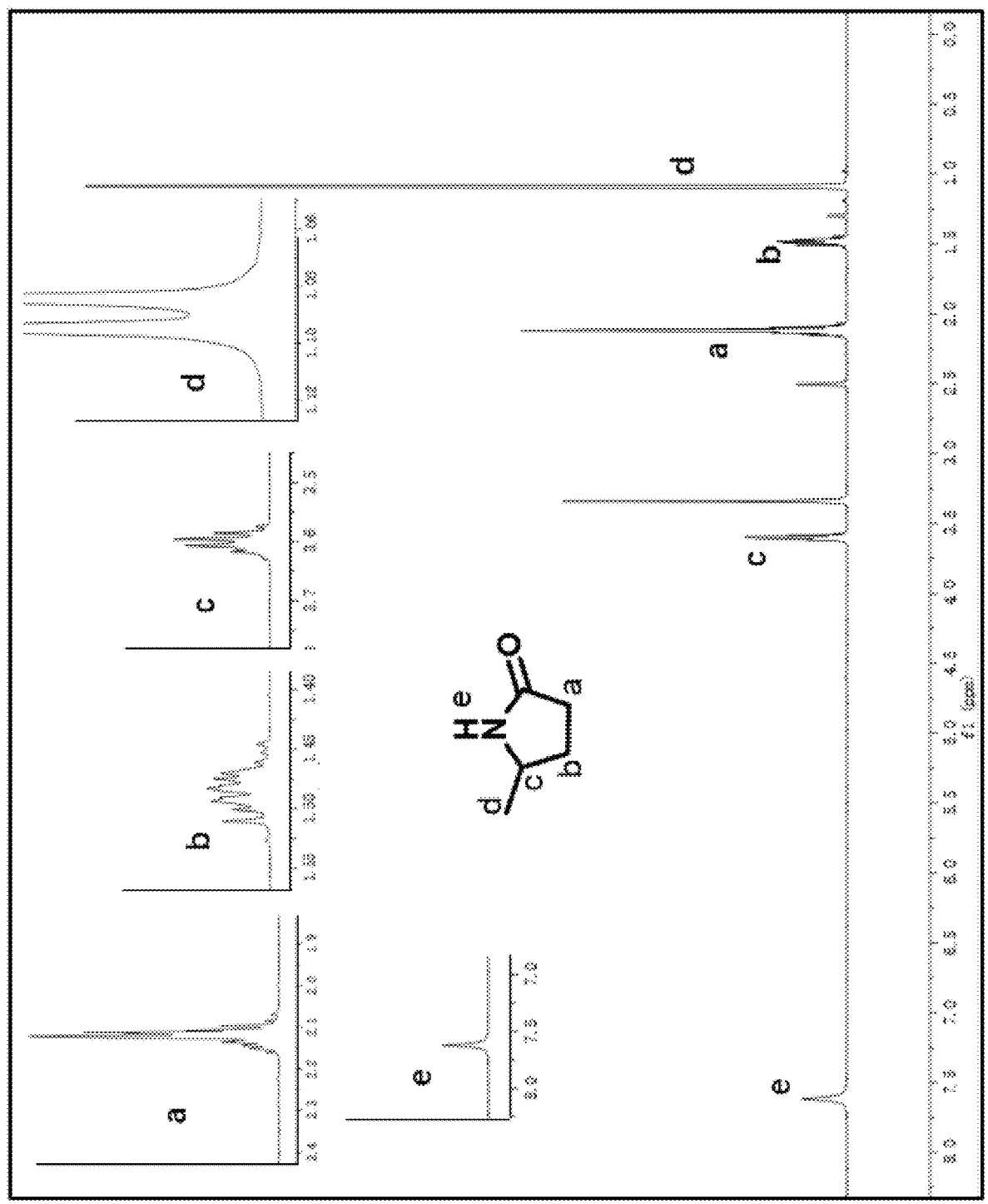
FIG. 2 shows a hydrogen spectrum of 5-methyl-2-pyrrolidone in Example 1.
Figure 3:
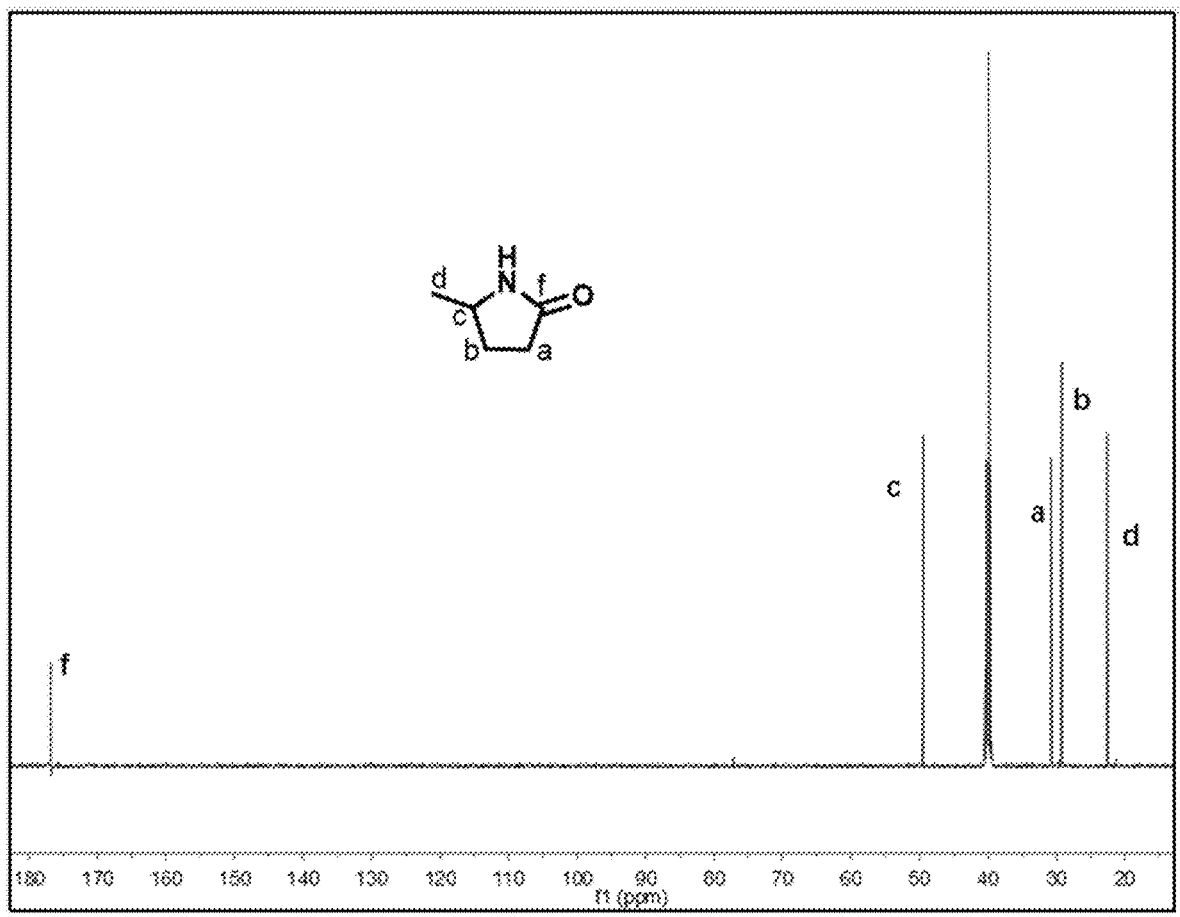
FIG. 3 shows a carbon spectrum of 5-methyl-2-pyrrolidone in Example 1.

A standard curve was made by using naphthalene as an internal standard. The yield of 5-methyl-2-pyrrolidone in the reaction solution detected by gas chromatography was 94%. The mass spectrum of the purified 5-methyl-2-pyrrolidone is shown in FIG. 1, with a molecular ion peak m/z: 99.1. Assignments of the hydrogen and carbon spectra are shown in FIG. 2 and FIG. 3, respectively. The conversion rate of levulinic acid was 100%.

Example 2

Synthesis of 5-(4-chlorophenyl)-2-pyrrolidone 2 mmol of 3-(4-chlorobenzoyl)propionic acid, 20 mmol of formamide and 80 mmol of water were put into a 15 mL polytetrafluoroethylene-lined stainless steel reactor, the sealed reactor was then placed in an oil bath pot heated to a predetermined temperature (180° C.) to carry out a reaction for 120 min at 500 r/min, and the reactor was then taken out and cooled to room temperature with tap water. 13 mL of methanol was put into the reactor, the yield of 5-(4-chlorophenyl)-2-pyrrolidone was measured by GC, and the conversion rate of 3-(4-chlorobenzoyl)propionic acid was measured by HPLC.

A standard curve was made by using naphthalene as an internal standard. The yield of 5-(4-chlorophenyl)-2-pyrrolidone (m/z: 194.1) in the mixed reaction solution detected by gas chromatography was 86%, and the conversion rate of 3-(4-chlorobenzoyl)propionic acid detected by liquid chromatography was 100%.

Example 3

Synthesis of 5-phenyl-2-pyrrolidone 2 mmol of 3-benzoylpropionic acid, 20 mmol of formamide, and 60 mmol of water were put into a 15 mL polytetrafluoroethylene-lined stainless steel reactor, the sealed reactor was then placed in an oil bath pot heated to a predetermined temperature (160° C.) to carry out a reaction for 240 min at 500 r/min, and the reactor was then taken out and cooled to room temperature with tap water. 13 mL of methanol was put into the reactor, the yield of 5-phenyl-2-pyrrolidone was measured by GC, and the conversion rate of 3-benzoylpropionic acid was measured by HPLC.

A standard curve was made by using naphthalene as an internal standard. The yield of 5-phenyl-2-pyrrolidone (m/z: 161.1) in the mixed reaction solution detected by gas chromatography was 81%, and the conversion rate of 3-benzoylpropionic acid detected by liquid chromatography was 100%.

Example 4

Synthesis of 5-(4-fluorophenyl)-2-pyrrolidone 2 mmol of 3-(4-fluorobenzoyl)propionic acid, 20 mmol of formamide, and 80 mmol of water were put into a 15 mL polytetrafluoroethylene-lined stainless steel reactor, the sealed reactor was then placed in an oil bath pot heated to a predetermined temperature (180° C.) to carry out a reaction for 120 min at 500 r/min, and the reactor was then taken out and cooled to room temperature with tap water. 13 mL of methanol was put into the reactor, the yield of 5-(4-fluorophenyl)-2-pyrrolidone was measured by GC, and the conversion rate of 3-(4-fluorobenzoyl)propionic acid was measured by HPLC.

A standard curve was made by using naphthalene as an internal standard. The yield of 5-(4-fluorophenyl)-2-pyrrolidone (m/z: 179.1) in the mixed reaction solution detected by gas chromatography was 87%, and the conversion rate of 3-(4-fluorobenzoyl)propionic acid detected by liquid chromatography was 100%.

Example 5

Synthesis of 5-(2-thienyl)-2-pyrrolidone 2 mmol of 4-oxo-4-(2-thienyl)butanoic acid, 10 mmol of formamide, and 40 mmol of water were put into a 15 mL polytetrafluoroethylene-lined stainless steel reactor, the sealed reactor was then placed in an oil bath pot heated to a predetermined temperature (160° C.) to carry out a reaction for 240 min at 500 r/min, and the reactor was then taken out and cooled to room temperature with tap water. 13 mL of methanol was put into the reactor, the yield of 5-(2-thienyl)-2-pyrrolidone was measured by GC, and the conversion rate of 4-oxo-4-(2-thienyl)butanoic acid was measured by HPLC.

A standard curve was made by using naphthalene as an internal standard. The yield of 5-(2-thienyl)-2-pyrrolidone (m/z: 167.1) in the mixed reaction solution detected by gas chromatography was 93%, and the conversion rate of 4-oxo-4-(2-thienyl)butanoic acid detected by liquid chromatography was 100%.

Example 6

Synthesis of 6-methyl-2-piperidone 2 mmol of acetobutyric acid, 10 mmol of formamide, and 40 mmol of water were put into a 15 mL polytetrafluoroethylene-lined stainless steel reactor, the sealed reactor was then placed in an oil bath pot heated to a predetermined temperature (160° C.) to carry out a reaction for 240 min at 500 r/min, and the reactor was then taken out and cooled to room temperature with tap water. 13 mL of methanol was put into the reactor, the yield of 6-methyl-2-piperidone was measured by GC, and the conversion rate of acetobutyric acid was measured by HPLC.

A standard curve was made by using naphthalene as an internal standard. The yield of 6-methyl-2-piperidone (m/z: 113.1) in the mixed reaction solution detected by gas chromatography was 92%, and the conversion rate of acetobutyric acid detected by liquid chromatography was 100%.

Example 7

Synthesis of 6-(4-fluorophenyl)-2-piperidone 2 mmol of 4-(4-fluorobenzoyl)butyric acid, 30 mmol of formamide, and 80 mmol of water were put into a 15 mL polytetrafluoroethylene-lined stainless steel reactor, the sealed reactor was then placed in an oil bath pot heated to a predetermined temperature (180° C.) to carry out a reaction for 60 min at 500 r/min, and the reactor was then taken out and cooled to room temperature with tap water. 13 mL of methanol was put into the reactor, the yield of 6-(4-fluorophenyl)-2-piperidone was measured by GC, and the conversion rate of 4-(4-fluorobenzoyl)butyric acid was measured by HPLC.

A standard curve was made by using naphthalene as an internal standard. The yield of 6-(4-fluorophenyl)-2-piperidone (m/z: 193.1) in the mixed reaction solution detected by gas chromatography was 70%, and the conversion rate of 4-(4-fluorobenzoyl)butyric acid detected by liquid chromatography was 100%.

Example 8

Synthesis of 6-phenyl-2-piperidone 2 mmol of 4-benzoyl butyric acid, 30 mmol of formamide and 80 mmol of water were put into a 15 mL polytetrafluoroethylene-lined stainless steel reactor, the sealed reactor was then placed in an oil bath pot heated to a predetermined temperature (180° C.) to carry out a reaction for 60 min at 500 r/min, and the reactor was then taken out and cooled to room temperature with tap water. 13 mL of methanol was put into the reactor, the yield of 6-phenyl-2-piperidone was measured by GC, and the conversion rate of 4-benzoyl butyric acid was measured by HPLC.

A standard curve was made by using naphthalene as an internal standard. The yield of 6-phenyl-2-piperidone (m/z: 175.1) in the mixed reaction solution detected by gas chromatography was 85%, and the conversion rate of 4-benzoyl butyric acid detected by liquid chromatography was 100%.

Example 9

Synthesis of 3-methyl-isoindole-1-one 2 mmol of 2-acetylbenzoic acid, 20 mmol of formamide, and 20 mmol of water were put into a 15 mL polytetrafluoroethylene-lined stainless steel reactor, the sealed reactor was then placed in an oil bath pot heated to a predetermined temperature (140° C.) to carry out a reaction for 300 min at 500 r/min, and the reactor was then taken out and cooled to room temperature with tap water. 13 mL of methanol was put into the reactor, the yield of 3-methyl-isoindole-1-one was measured by GC, and the conversion rate of 2-acetylbenzoic acid was measured by HPLC.

A standard curve was made by using naphthalene as an internal standard. The yield of 3-methyl-isoindole-1-one (m/z: 147.1) in the mixed reaction solution detected by gas chromatography was 80%, and the conversion rate of 2-acetylbenzoic acid detected by liquid chromatography was 100%.

What is claimed is:

1. A method for synthesizing lactam derivatives without use of a catalyst, comprising: carrying out a direct addition reaction between a raw material keto acid derivative and formamide functioning as both an amine source and a hydrogen source in the absence of an organic solvent or a catalyst, and then carrying out formic acid reduction and ring-closure reaction to obtain a corresponding lactam derivative.

2. The method for synthesizing lactam derivatives without use of a catalyst according to claim 1, wherein the preparation of the lactam derivative is carried out in water, the reaction system is a closed system, and the reaction is carried out for 60 to 300 min at a temperature within a range of 140° C. to 180° C.

3. The method for synthesizing lactam derivatives without use of a catalyst according to claim 1, wherein a molar ratio of the keto acid derivative to the formamide to water is 1:5~15:10~40.

4. The method for synthesizing lactam derivatives without use of a catalyst according to claim 1, wherein the keto acid derivative comprises levulinic acid, 3-(4-chlorobenzoyl)propionic acid, 3-benzoylpropionic acid, 3-(4-fluorobenzoyl)

propionic acid, 4-oxo-4-(2-thienyl)butanoic acid, acetobutyric acid, 4-(4-fluorobenzoyl)butyric acid, 4-benzoylbutyric acid, and 2-acetylbenzoic acid.

5. The method for synthesizing lactam derivatives without use of a catalyst according to claim 1, wherein the lactam derivatives synthesized comprise 5-methyl-2-pyrrolidone, 5-(4-chlorophenyl)-2-pyrrolidone, 5-phenyl-2-pyrrolidone, 5-(4-Fluorophenyl)-2-pyrrolidone, 5-(2-thienyl)-2-pyrrolidone, 6-methyl-2-piperidone, 6-(4-fluorophenyl)-2-piperidine ketone, 6-phenyl-2-piperidone, and 3-methyl-isoindol-1-one.

* * * * *